(12) United States Patent
Zhmayev et al.

(10) Patent No.: US 12,072,222 B2
(45) Date of Patent: Aug. 27, 2024

(54) ASSESSING A FLOW OF A SPRAYED COATING

(71) Applicant: BASF Coatings GmbH, Münster (DE)

(72) Inventors: Yevgen Zhmayev, Münster (DE); Fatmir Raka, Münster (DE); Igor Millbaier, Münster (DE)

(73) Assignee: BASF COATINGS GMBH, Muenster (DE)

( * ) Notice: Subject to any disclaimer, the term of this patent is extended or adjusted under 35 U.S.C. 154(b) by 255 days.

(21) Appl. No.: 17/779,350

(22) PCT Filed: Nov. 18, 2020

(86) PCT No.: PCT/EP2020/082606
§ 371 (c)(1),
(2) Date: May 24, 2022

(87) PCT Pub. No.: WO2021/104972
PCT Pub. Date: Jun. 3, 2021

(65) Prior Publication Data
US 2022/0404254 A1     Dec. 22, 2022

(30) Foreign Application Priority Data
Nov. 27, 2019  (EP) .................................. 19211932

(51) Int. Cl.
*G01N 21/84* (2006.01)
*G01F 1/7086* (2022.01)
(Continued)

(52) U.S. Cl.
CPC .......... *G01F 1/7086* (2013.01); *G01N 11/00* (2013.01); *G01N 21/8422* (2013.01);
(Continued)

(58) Field of Classification Search
CPC ....... G01F 1/7086; G01F 1/704; G01N 11/00; G01N 21/8422; G01N 2011/008;
(Continued)

(56) References Cited

U.S. PATENT DOCUMENTS 7,763,325 B1 * 7/2010 Paxson ................... C23C 4/129
427/455
2004/0245354 A1 * 12/2004 Srinivasan .............. C23C 24/04
239/74

(Continued)

FOREIGN PATENT DOCUMENTS

EP     0926254 A2   6/1999
JP     H10221357 A  8/1998
(Continued)

OTHER PUBLICATIONS

International Search Report and Written Opinion for corresponding PCT/EP2020/082606 mailed Jan. 25, 2021, 8 Pages.

*Primary Examiner* — Suman K Nath
(74) *Attorney, Agent, or Firm* — Armstrong Teasdale LLP

(57) ABSTRACT

Disclosed herein is a method for assessing a flow a sprayed coating, including the steps of spraying a coating onto a surface and capturing a plurality of images of the sprayed surface at a predetermined frequency within a predetermined interval of time, and a computer program product for assessing a flow of a sprayed coating.

15 Claims, 4 Drawing Sheets

(51) Int. Cl.
*G01N 11/00* (2006.01)
*G06T 7/00* (2017.01)
(52) U.S. Cl.
CPC ........ G06T 7/001 (2013.01); *G01N 2011/008* (2013.01); *G01N 2021/8427* (2013.01); *G06T 2207/30156* (2013.01)
(58) Field of Classification Search
CPC .......... G01N 2021/8427; G01N 33/208; G06T 7/001; G06T 2207/30156; C23C 4/00; C23C 24/00; G01P 5/20; G01P 13/0093
See application file for complete search history.

(56) References Cited

U.S. PATENT DOCUMENTS

| | | | |
|---|---|---|---|
| 2007/0248744 A1* | 10/2007 | Wintergerste | ........... C23C 24/04 118/620 |
| 2008/0312892 A1 | 12/2008 | Heggemann | |
| 2014/0011040 A1* | 1/2014 | Decker | ................... C23C 24/10 427/195 |

FOREIGN PATENT DOCUMENTS

| | | |
|---|---|---|
| JP | 2011180028 A | 9/2011 |
| WO | 2013141915 A1 | 9/2013 |

* cited by examiner

ASSESSING A FLOW OF A SPRAYED COATING

CROSS-REFERENCE TO RELATED APPLICATIONS

This application is a U.S. National Phase Application of International Patent Application No. PCT/EP2020/082606, filed Nov. 18, 2020, which claims priority to European Patent Application No. 19211932.9, filed Nov. 27, 2019, each of which is hereby incorporated by reference herein.

FIELD OF THE INVENTION

The invention relates to a method for assessing a flow of a sprayed coating. The method comprises the steps of spraying a coating onto a surface and capturing a plurality of images of the sprayed surface at a predetermined frequency within a predetermined interval of time. The invention further relates to a computer program product for assessing a flow of a sprayed coating.

BACKGROUND

Surfaces of devices are coated mostly for aesthetic and protective reasons. The coating may provide a device with an intended color or texture on the one hand. On the other hand the coating may prevent the device from wear and, in particular, from corrosion in case the surface of the device is made from a corrosive material like a metal. Both effects are particularly important in car manufacturing where most of car body parts are coated.

A surface is usually coated by spraying a liquid coating onto the surface. The coating initially contains a volatile solvent rendering the coating liquid for spraying. After having been sprayed onto the surface the solvent gradually evaporates from the sprayed coating causing the coating to set on the surface. Finally, the coating may be cured by applying an ultraviolet light and/or a heat to the sprayed coating.

A quality of a coated surface depends on two parameters of the coating called sagging and leveling. Sagging indicates the ability of adjacent layers of the coating to displace relative to each other. The higher the sagging of the coating is the less the layers of the coating adhere to each other and, as a consequence, the worse the coating is. Leveling indicates a smoothness of a surface of the coating. The higher the leveling of the coating is the smoother the surface of the coating is and, as a consequence, the better the coating is. Thus, a coating having a low sagging and a high leveling is aimed at.

However, the sprayed coating is exposed to a gravity continuously during gradual evaporation of the solvent. The gravity may and usually does cause the still liquid coating to flow on the surface when setting, wherein the coating flows in a direction defined by a shape of the surface and an orientation of the surface relative to the gravity.

The gravity, thus, may easily deteriorate a quality of the coating by causing a sagging of the sprayed coating and preventing the sprayed coating from leveling.

SUMMARY OF THE INVENTION

It is therefore an object of the invention to propose a method for assessing a flow of a sprayed coating which assessment allows for reducing a sagging of the coating and increasing a leveling of the coating. Another object of the invention is to provide a computer program product for assessing a flow of a sprayed coating.

One aspect of the invention is a method for assessing a flow of a sprayed coating, comprising the steps of spraying a coating onto a surface, capturing a plurality of images of the sprayed surface at a predetermined frequency within a predetermined interval of time. The plurality of images form an ordered sequence of images representing a temporal change of the sprayed coating during the predetermined interval of time.

According to the invention, the method comprises the steps of providing a coating with a plurality of tracer particles, spraying the provided coating onto a surface, processing each captured image and deriving at least one flow parameter of the sprayed coating from tracer particles imaged by the plurality of processed images. The tracer particles are added to the coating for the assessment only, i.e. the tracer particles are not an original component of the coating.

A color, a reflectivity, a size and the like of the tracer particles may be chosen to render the tracer particles visually distinguishable from the coating. When the sprayed coating flows on the surface the tracer particles are driven by the flowing sprayed coating. The tracer particles must not be chosen to move relative to the sprayed coating on their own in order to obtain an accurate result of the assessment.

In a preferred embodiment each image is captured by a camera with an optical axis extending onto the coated surface. In other words, the position and the orientation of the camera support capturing images of the sprayed surface.

Advantageously, a white board having a line pattern is illuminated by a white light source and the white board is reflected by the sprayed surface parallel to the optical axis of the camera. In other words, the captured image comprises the reflected line pattern in form of relatively darker regions. The line pattern may comprise a plurality of lines, particularly a plurality of parallel lines, more particularly a plurality of parallel lines being arranged at equal distances. Alternatively, the line pattern may comprise a grid, i.e. a plurality of crossing lines, particularly a regular rectangular grid having a plurality of equally spaced parallel lines extending perpendicular to another plurality of equally spaced parallel lines. The reflected line pattern supports a localization of tracer particles within a captured image.

It is preferred that processing each image comprises highlighting at least one tracer particle in the image. The highlighting may comprise increasing a contrast of the image, coloring the at least one tracer particle differently, increasing a size of the at least one tracer particle in the image and the like. The highlighting may be considered as a part of a preprocessing of the image and facilitates an automatic recognition of the at least one tracer particle.

Processing each image may comprise using an existing software tool for image processing. Accordingly, image processing may be carried out by means of standard software without any need for dedicated customization.

In advantageous embodiments deriving at least one flow parameter comprises recognizing at least one tracer particle in the image by applying a pattern recognition algorithm. The tracer particles appear to be discrete pointlike objects in the image which differ from the surrounding coating. As a consequence, the tracer particles may be easily recognized by means of pattern recognition.

Deriving at least one flow parameter preferably comprises determining a position of at least one tracer particle in each image. The position may be determined by image coordinates or, if applicable, by coordinates defined by the line pattern.

In further embodiments a time dependency of the position of the at least one tracer particle is derived as the at least one flow parameter. The time dependency of the position is derived by analyzing the ordered sequence of images and identifying the at least one tracer particle and its possibly varying position in each image.

Time dependencies of positions of a plurality of tracer particles are advantageously averaged with respect to the tracer particles and the averaged time dependency of positions is derived as the at least one flow parameter.

Thereby the averaging may be accomplished with respect to a plurality of tracer particles in the same ordered sequence of images and/or with respect to a plurality of tracer particles in different ordered sequences of images. The averaged time dependency may provide a higher reliability than the positional time dependency of a single tracer particle.

Alternatively or additionally, deriving at least one flow parameter may comprise determining a velocity of at least one tracer particle in the plurality of images. The velocity may be calculated, i.e. approximated, by multiplying the positional difference of the tracer particle in successive images with the predetermined frequency.

In still further embodiments a time dependency of the velocity of the at least one tracer particle is derived as the at least one flow parameter. The time dependency of the velocity is derived by analyzing the ordered sequence of images and identifying the at least one tracer particle and its possibly varying velocity in each image.

Time dependencies of velocities of a plurality of tracer particles are advantageously averaged with respect to the tracer particles and the averaged time dependency of velocities is derived as the at least one flow parameter. The averaged time dependency may provide a higher reliability than the time dependency of a single tracer particle.

In many embodiments the predetermined interval of time is in a range from 300 s to 1000 s, preferably in a range from 450 s to 625 s and most preferably is 500 s and/or the predetermined frequency is in a range from 0.05 $s^{-1}$ to 1 $s^{-1}$, preferably in a range from 0.1 $s^{-1}$ to 0.5 $s^{-1}$ and most preferably is 0.2 $s^{-1}$. For example, it is preferred to capture 100 images within 500 s.

In many embodiments the method is carried out by a processor executing a program code implementing the method. In this way assessing the flow of the sprayed coating may be automated at least partially which increases an efficiency and accuracy of the assessing process.

Another aspect of the invention is a computer program product for assessing a flow of a sprayed coating, comprising a data carrier storing a program code to be executed by a processor. The data carrier may be used for installing the stored program code and/or for upgrading an installed program code with the stored program code.

According to the invention, the program code implements an inventive method. The stored program code enables for efficiently assessing of a sagging and/or leveling of a coating and, thus, optimizing a quality of coating.

It is an essential advantage of the method according to the invention that a flow of a sprayed coating is assessed very easily and precisely. The method allows for deriving different flow parameters of the sprayed coating by using a simple arrangement of existing devices and established algorithms of image processing.

Further advantages and configurations of the invention become apparent from the following description and the enclosed drawings.

It shall be understood that the features described previously and to be described subsequently may be used not only in the indicated combinations but also in different combinations or on their own without leaving the scope of the present invention.

DETAILED DESCRIPTION OF THE DRAWINGS

Figure 1:
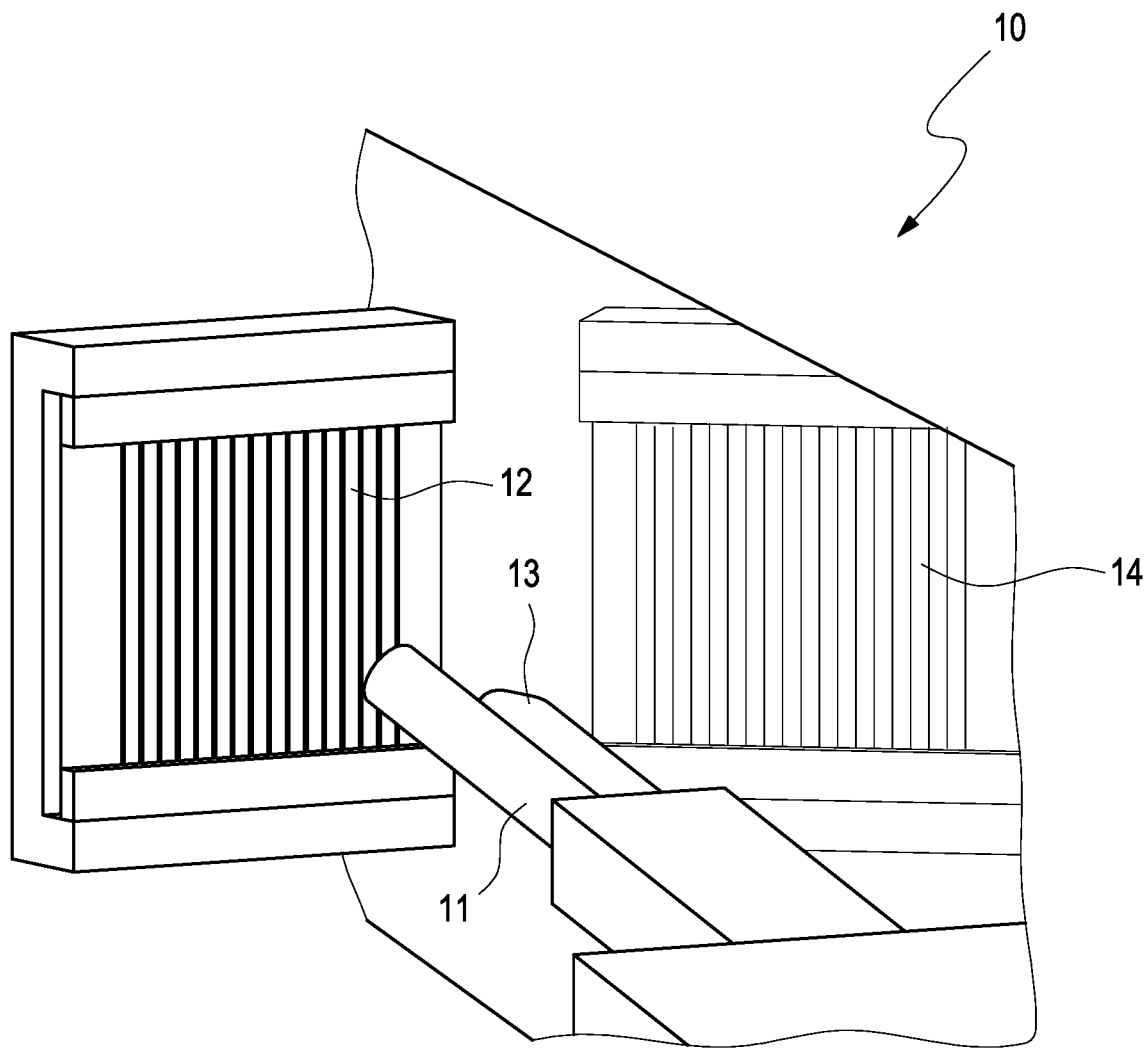
FIG. 1 schematically shows a perspective view of an arrangement for carrying out a method according to an embodiment of the invention.

FIG. 1 schematically shows a perspective view of an arrangement 10 for carrying out a method according to an embodiment of the invention. The arrangement 10 comprises a sprayed surface 14 and a camera 13 with an optical axis extending onto the sprayed surface 14, i.e. the camera 13 is directed to the sprayed surface 14. The arrangement 10 may further comprise a white board 12 having a line pattern and a light source 11 being arranged for illuminating the white board 12.

The camera 13, the sprayed surface 14 and the white board 12 are preferably arranged relative to each other such that the line pattern of the white board 12 is reflected by the sprayed surface 14 parallel to the optical axis of the camera 13 into the camera 13. The line pattern may comprise a plurality of equally spaced parallel lines or preferably a rectangular grid of equally spaced parallel lines (see FIGS. 2 and 3).

A flow of the sprayed coating is assessed by applying the following method steps. A coating is provided with a plurality of tracer particles and sprayed onto the surface 14. Then the camera 13 captures a plurality of images 20 of the sprayed surface 14 at a predetermined frequency within a predetermined interval of time.

The predetermined interval of time may be in a range from 300 s to 1000 s, preferably in a range from 450 s to 625 s and exemplarily is 500 s. The predetermined frequency may be in a range from 0.05 $s^{-1}$ to 1 $s^{-1}$, preferably in a range from 0.1 $s^{-1}$ to 0.5 $s^{-1}$ and exemplarily is 0.2 $s^{-1}$. The captured images 20, thus, form an ordered sequence of images 20.

Figure 2:
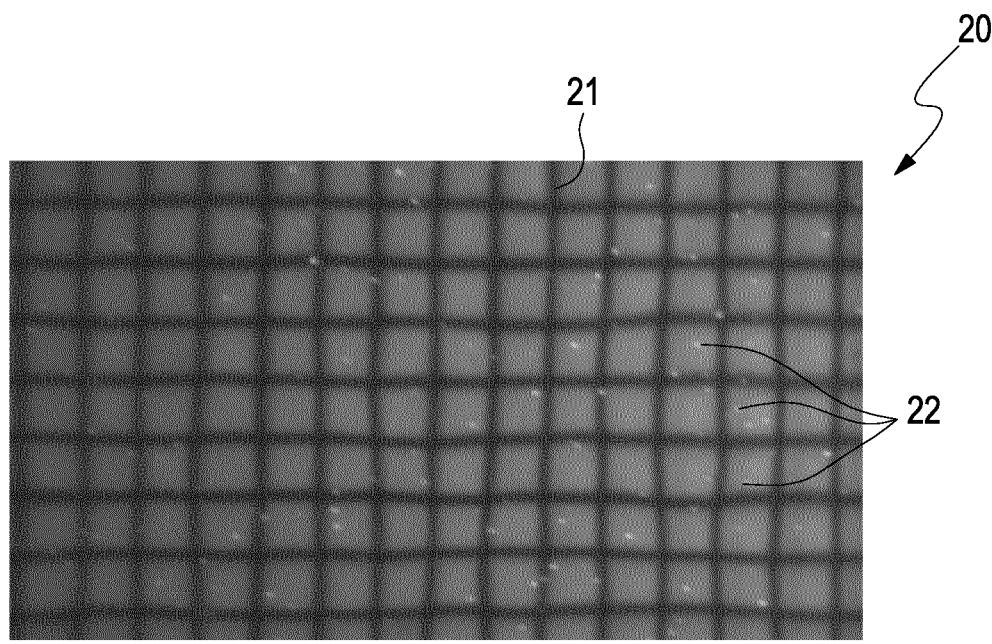
FIG. 2 schematically shows schematically an image captured in a method according to an embodiment of the invention.

FIG. 2 schematically shows schematically an image 20 captured in a method according to an embodiment of the invention. The image 20 comprises a plurality of point-like tracer particles 22 and a reflected rectangular grid 21 of equally spaced parallel lines.

Each captured image 20 is processed by using an existing software tool for image processing. Processing each image 20 may comprise highlighting at least one tracer particle 22, preferably a plurality of tracer particles 22 in the image 20.

Figure 3:
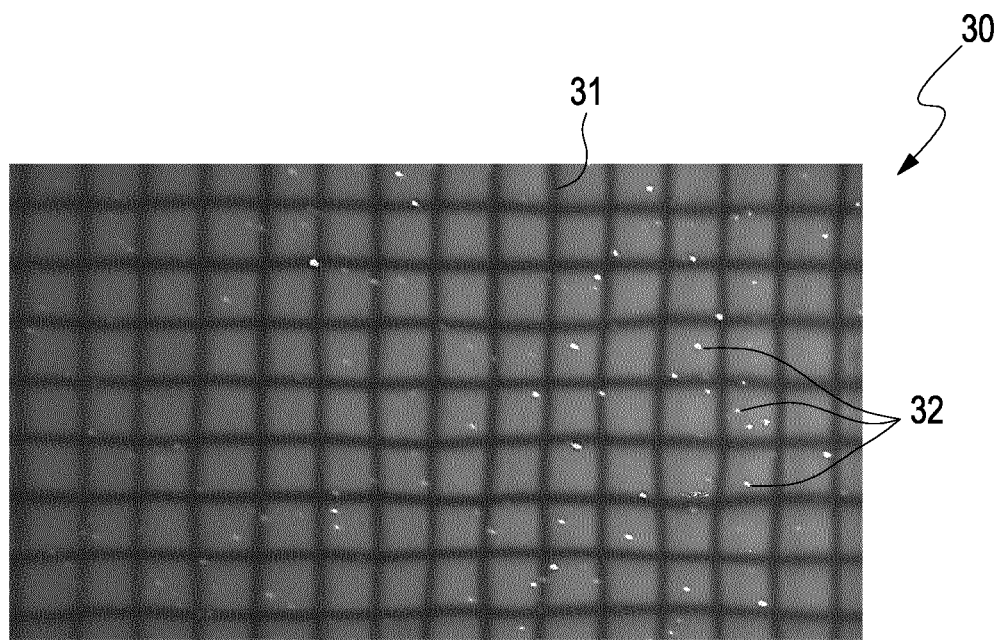
FIG. 3 schematically shows schematically the processed image corresponding to the captured image shown in FIG. 2.

FIG. 3 schematically shows schematically a processed image 30 corresponding to the captured image 20 shown in FIG. 2. The image comprises a plurality of highlighted tracer particles 32 and the rectangular grid 31 of lines.

At least one flow parameter of the sprayed coating is derived from the plurality of tracer particles 32 imaged by the plurality of processed images 30. Deriving the at least one flow parameter comprises recognizing a plurality of tracer particles 32 in the image 30 by applying a pattern recognition algorithm. Deriving the at least one flow parameter further comprises determining respective positions 43 of the plurality of tracer particles 32 in each image 30.

The positions 43 of the tracer particles 32 may be determined with respect to the grid 31 or to a coordinate system of the image 30, i.e. in image coordinates.

A time dependency of the positions 43 of the plurality of tracer particles 32 may be derived as a first flow parameter from the plurality of processed images 30.

Figure 4:
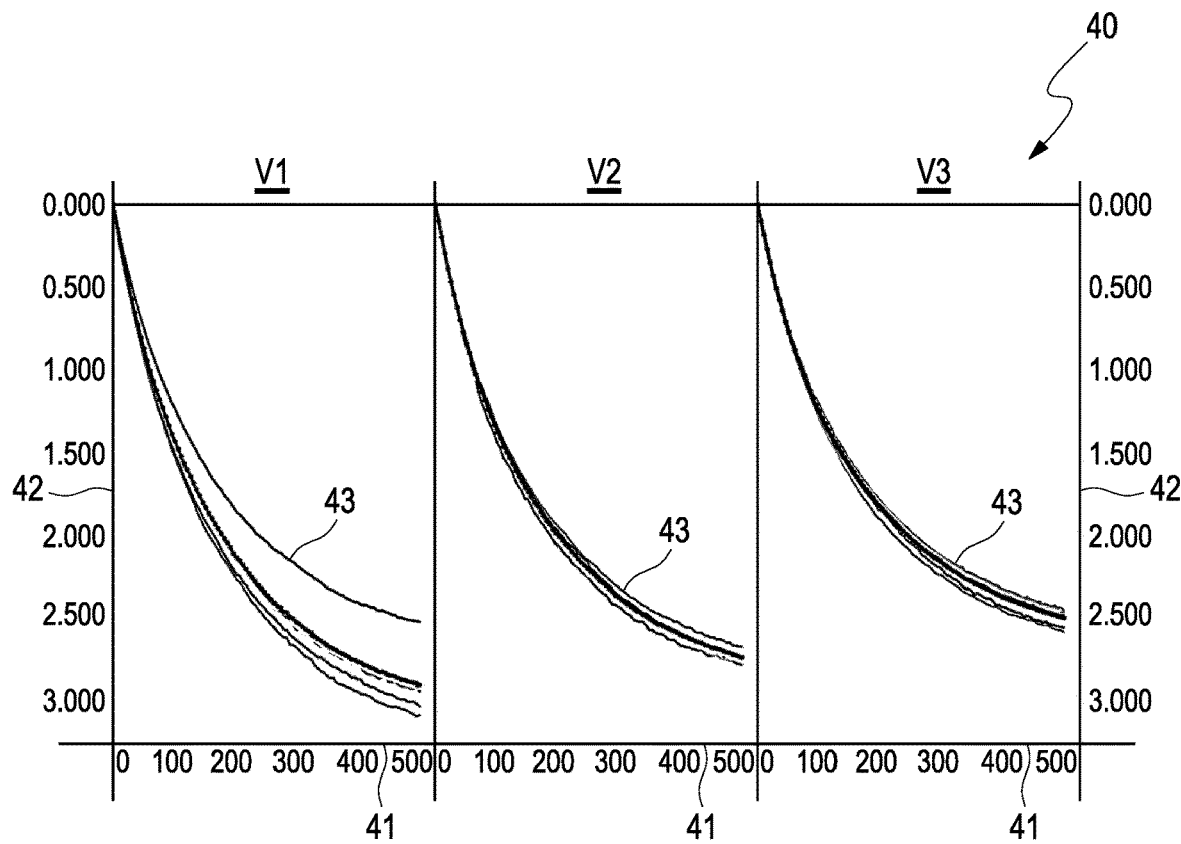
FIG. 4 shows a graph of positions of tracer particles.

FIG. 4 shows a graph 40 of positions 43 of tracer particles 32. The graph 40 comprises three segments V1, V2, V3 and may be considered to represent a first sagging profile of the sprayed coating. Each segment has an abscissa 41 indicating times of the images 30 and an ordinate 42 indicating sagging positions 43 of the tracer particles 32. The abscissas 41 cover a time interval of 500 s, respectively. The ordinates 42 cover positions in a range from 0 mm to 3 mm. The segments V1, V2 illustrate sagging positions of 5 tracer particles 32 while the segment V3 illustrates sagging positions of 6 tracer particles 32. It can be observed from graph 40 that the positions 43 of the tracer particles 32 sag, i.e. get lower, starting from a position which is shown by the first image 30 and equally set to zero for each tracer particle 32 and that the respective positional variations decrease as the coating sets. Another observation is a positional spread between the tracer particles 32.

Time dependencies of the positions 43 of the plurality of tracer particles 32 may be averaged with respect to the tracer particles 32 and the averaged time dependency of positions may be derived as a second flow parameter.

Figure 5:
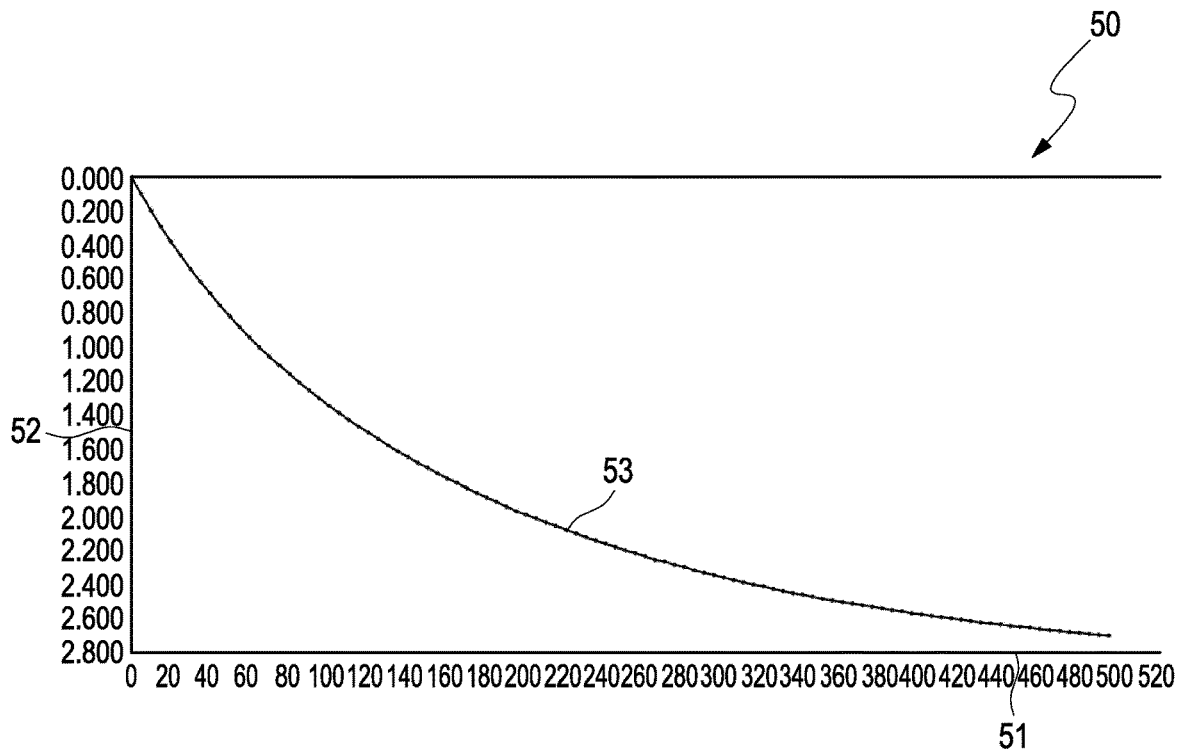
FIG. 5 shows a graph of averaged positions of tracer particles.

FIG. 5 shows a graph 50 of averaged positions 53 of tracer particles 32. The graph 50 has an abscissa 51 indicating times of the images 30 and an ordinate 52 indicating averaged sagging positions 53 of the tracer particles 32. The abscissa 51 covers a time interval of 500 s. The ordinate 52 covers sagging positions in a range from 0 mm to 2.8 mm.

Deriving at least one flow parameter may further comprise determining velocities 63 of the plurality of tracer particle 32 in the plurality of images 30.

A time dependency of the velocities 63 of the plurality of tracer particles 32 may be derived as a third flow parameter.

Figure 6:
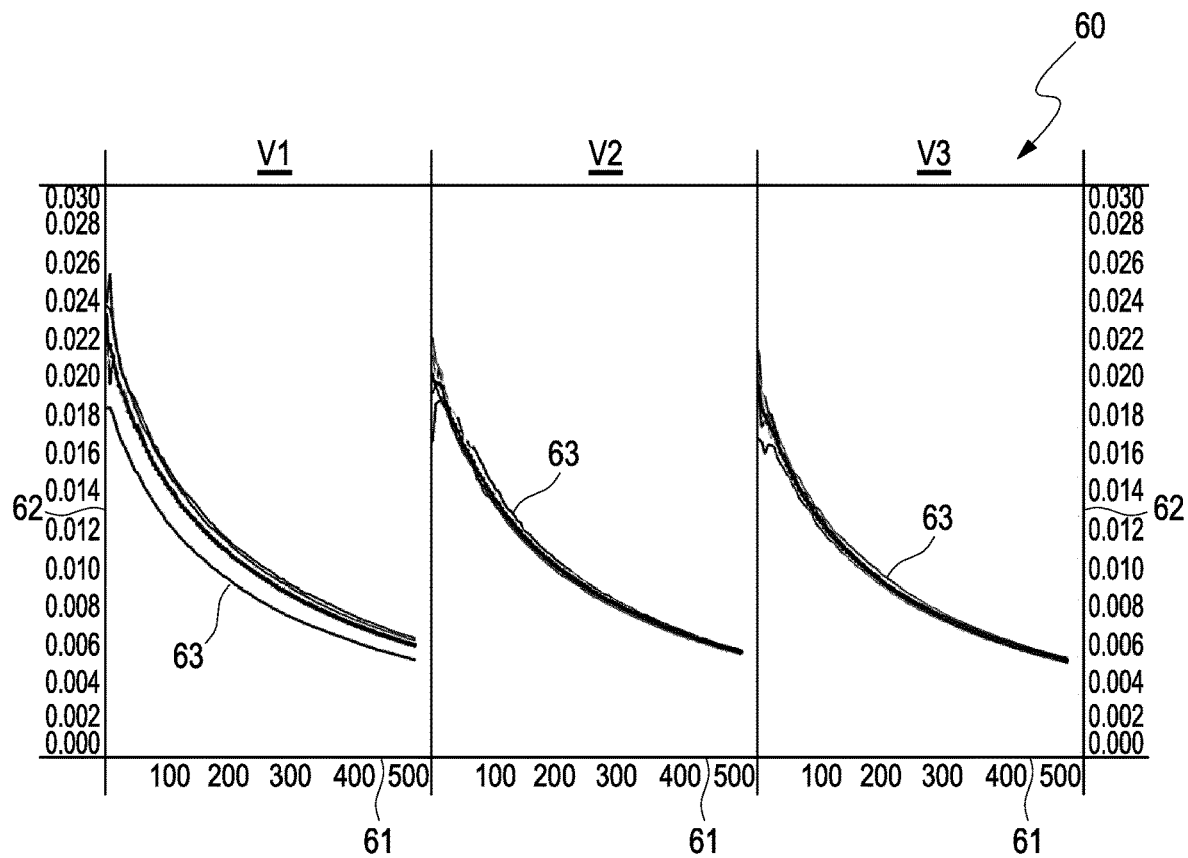
FIG. 6 shows a graph of velocities of tracer particles.

FIG. 6 shows a graph 60 of velocities 63 of tracer particles 32. The graph 60 comprises three segments V1, V2, V3 and may be considered to represent a second sagging profile of the sprayed coating. Each segment has an abscissa 61 indicating times of the images 30 and an ordinate 62 indicating sagging velocities 63 of the tracer particles 32. The abscissas 61 cover a time interval of 500 s, respectively. The ordinates 62 cover velocities in a range from 0.03 mms$^{-1}$ to 0 mms$^{-1}$. The segments V1, V2 illustrates sagging velocities 63 of 5 tracer particles 32 while the segment V3 illustrates sagging velocities 63 of 6 tracer particles 32. It can be observed from graph 60 that the sagging velocities 63 of the tracer particles 32 and the respective sagging velocity variations decrease as the coating sets. Another observation is a velocity spread between the tracer particles 32.

Time dependencies of velocities 63 of a plurality of tracer particles 32 may be averaged with respect to the tracer particles 32 and the averaged time dependency of velocities 63 may be derived as a fourth flow parameter.

Figure 7:
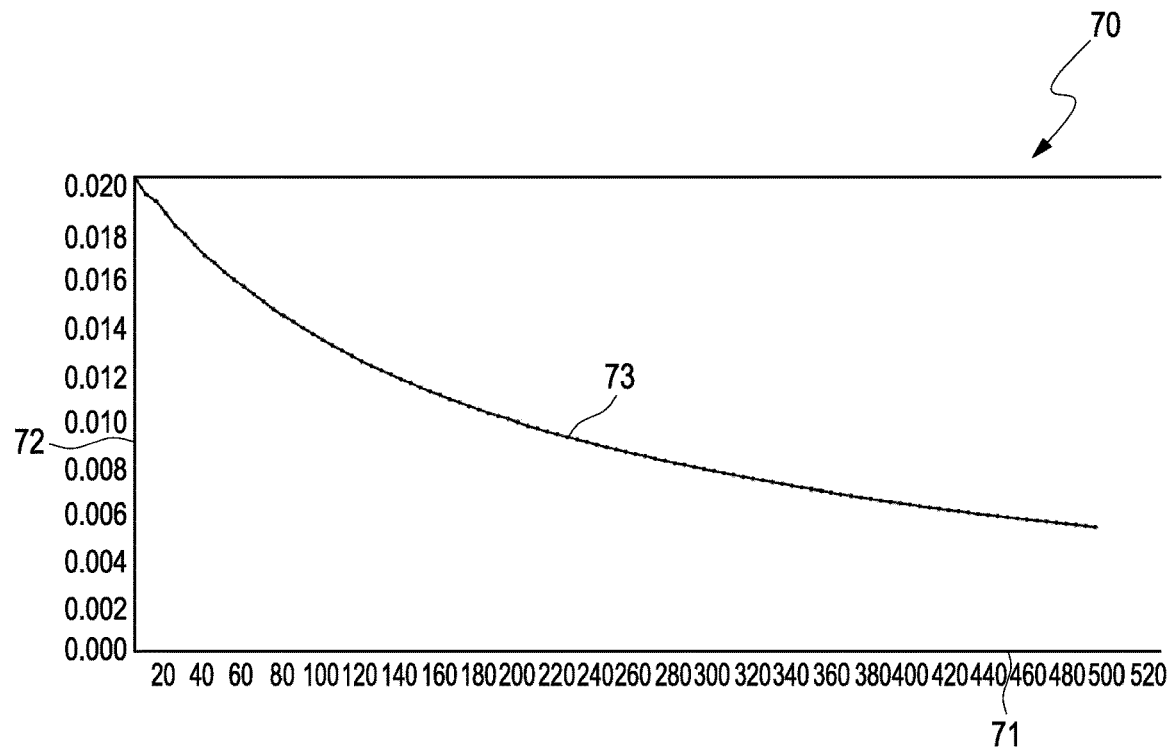
FIG. 7 shows a graph of averaged velocities of tracer particles.

FIG. 7 shows a graph 70 of averaged velocities 73 of tracer particles 32. The graph 70 has an abscissa 71 indicating times of the images 30 and an ordinate 72 indicating averaged sagging velocities 73 of the tracer particles 32. The abscissa 71 covers a time interval of 500 s. The ordinate 72 covers sagging velocities in a range from 0.02 mms$^{-1}$ to 0 mms$^{-1}$.

The method is preferably carried out by a processor executing a program code implementing the method wherein the program code may be stored on a data carrier of a computer program product for assessing a flow of a sprayed coating and have been installed from the data carrier.

REFERENCE NUMERALS 10 arrangement
11 light source
12 white board
13 camera
14 sprayed surface
20 captured image
21 grid
22 tracer particle
30 processed image
31 grid
32 tracer particle
40 graph
41 abscissa
42 ordinate
43 position of a tracer particle
50 graph
51 abscissa
52 ordinate
53 averaged position of tracer particles
60 graph
61 abscissa
62 ordinate
63 velocity of a tracer particle
70 graph
71 abscissa
72 ordinate
73 averaged velocity of tracer particles

The invention claimed is:

1. A method for assessing a flow of a sprayed coating, comprising the steps of:
   providing a coating with a plurality of tracer particles;
   spraying the provided coating onto a surface;
   capturing a plurality of images of the sprayed surface at a predetermined frequency within a predetermined interval of time;
   processing each captured image; and
   deriving at least one flow parameter of the sprayed coating from tracer particles imaged by the plurality of processed images.

2. The method according to claim 1, wherein processing each image comprises highlighting at least one tracer particle in the image.

3. The method according to claim 1, wherein processing each image comprises using an existing software tool for image processing.

4. The method according to claim 1, wherein deriving at least one flow parameter comprises recognizing at least one tracer particle in the image by applying a pattern recognition algorithm.

5. The method according to claim 1, wherein deriving at least one flow parameter comprises determining a position of at least one tracer particle in each image.

6. The method according to claim 5, wherein a time dependency of the position of the at least one tracer particle is derived as the at least one flow parameter.

7. The method according to claim 6, wherein time dependencies of the positions of a plurality of tracer particles are averaged with respect to the tracer particles and the averaged time dependency of the positions is derived as the at least one flow parameter.

8. The method according to claim 1, wherein deriving at least one flow parameter comprises determining a velocity of at least one tracer particle in the plurality of images.

9. The method according to claim 8, wherein a time dependency of the velocity of the at least one tracer particle is derived as the at least one flow parameter.

10. The method according to claim 9, wherein time dependencies of the velocities of a plurality of tracer particles are averaged with respect to the tracer particles and the averaged time dependency of the velocities is derived as the at least one flow parameter.

11. The method according to claim 1, wherein the predetermined interval of time is in a range from 300 s to 1000 s and/or the predetermined frequency is in a range from 0.05 s−1 to 1 s−1.

12. The method according to claim 1, wherein the method is carried out by a processor executing a program code implementing the method.

13. A computer program product for assessing a flow of a sprayed coating, comprising a data carrier storing a program code to be executed by a processor, the program code implementing a method according to claim 1.

14. The method according to claim 1, wherein the predetermined interval of time is in a range from 450 s to 625 and/or the predetermined frequency is in a range from 0.1 s−1 to 0.5 s−1.

15. The method according to claim 1, wherein the predetermined interval of time is 500 s and/or the predetermined frequency is 0.2 s−1.

* * * * *